United States Patent [19]

Mohnsen et al.

[11] Patent Number: 4,804,268

[45] Date of Patent: Feb. 14, 1989

[54] METHOD OF MEASURING THE INTERACTION BETWEEN WALLS AND FLUID

[75] Inventors: Helmut M. Mohnsen, Ismaning; Benno Reuter, Oberschleissheim; Wulfram Schauerte, Grafrath/Wiedenroth, all of Fed. Rep. of Germany

[73] Assignee: Gesellschaft für Strahlen-und Umweltforschung mbH, Neuherberg, Fed. Rep. of Germany

[21] Appl. No.: 938,719

[22] Filed: Dec. 5, 1986

[30] Foreign Application Priority Data

Dec. 6, 1985 [DE] Fed. Rep. of Germany ....... 3543108

[51] Int. Cl.$^4$ ..................... G01N 13/00; G01N 11/04; G01N 21/41; G01N 21/47
[52] U.S. Cl. ...................................... 356/338; 356/28
[58] Field of Search ..................... 356/27, 28, 336, 338

[56] References Cited

U.S. PATENT DOCUMENTS

| | | | |
|---|---|---|---|
| 3,975,084 | 8/1976 | Block | 356/244 |
| 4,385,830 | 5/1983 | Webb et al. | 356/338 |
| 4,608,344 | 8/1986 | Carter et al. | 356/414 |
| 4,664,513 | 5/1987 | Webb et al. | 356/28 |

FOREIGN PATENT DOCUMENTS

| | | |
|---|---|---|
| 0044730 | 1/1982 | European Pat. Off. . |
| 2929018 | 2/1981 | Fed. Rep. of Germany . |
| 978046 | 11/1982 | U.S.S.R. . |

OTHER PUBLICATIONS

Wilks, Paul, "Internal Reflection Spectroscopy", *International Laboratory* (Jul./Aug. 1980).

*Primary Examiner*—Richard A. Rosenberger
*Attorney, Agent, or Firm*—Spencer & Frank

[57] ABSTRACT

A method of measuring the interaction of a fluid with a wall bounding the fluid which method includes placing tracer particles in the fluid, illuminating the particles, and measuring the movement of the particles by means of scattered light, the improvement wherein the step of illuminating comprises illuminating a region of the fluid adjacent the wall at a distance of less than about 1 micron from the wall with a light beam directed towards the interface of the fluid and the wall so that the light beam is completely reflected; and the step of measuring comprises recording the scattered light images resulting from the motion of the tracer particles in the region and evaluating the motion of the fluid adjacent the wall. The invention also describes an apparatus for practicing the novel method.

6 Claims, 4 Drawing Sheets

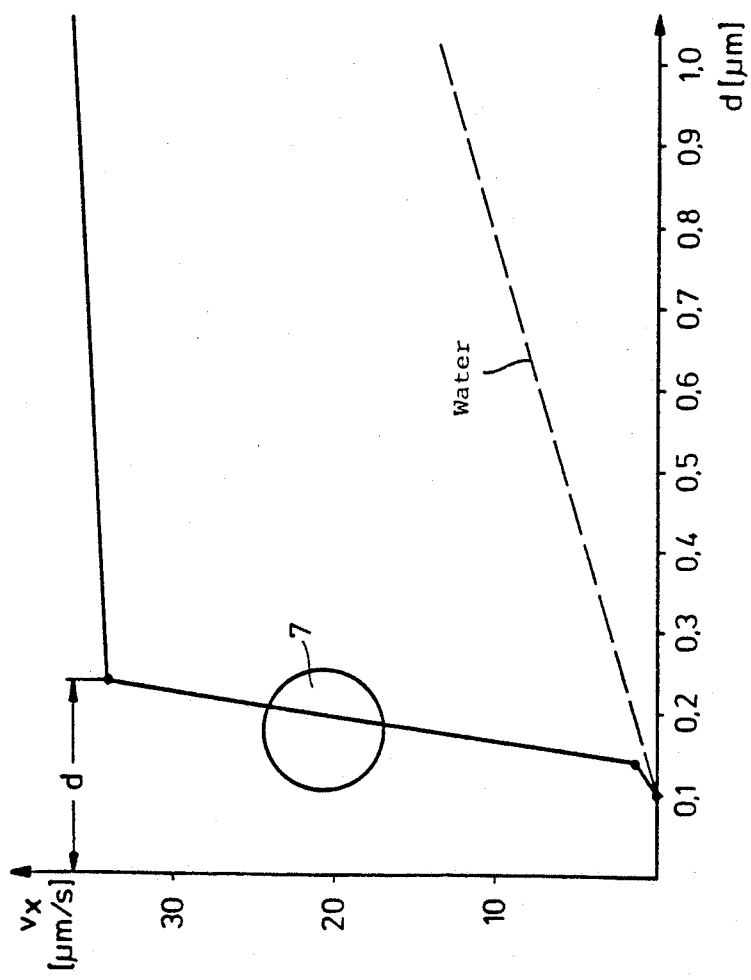

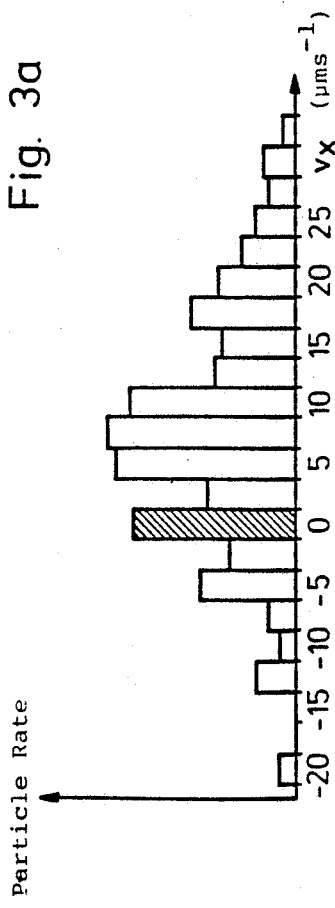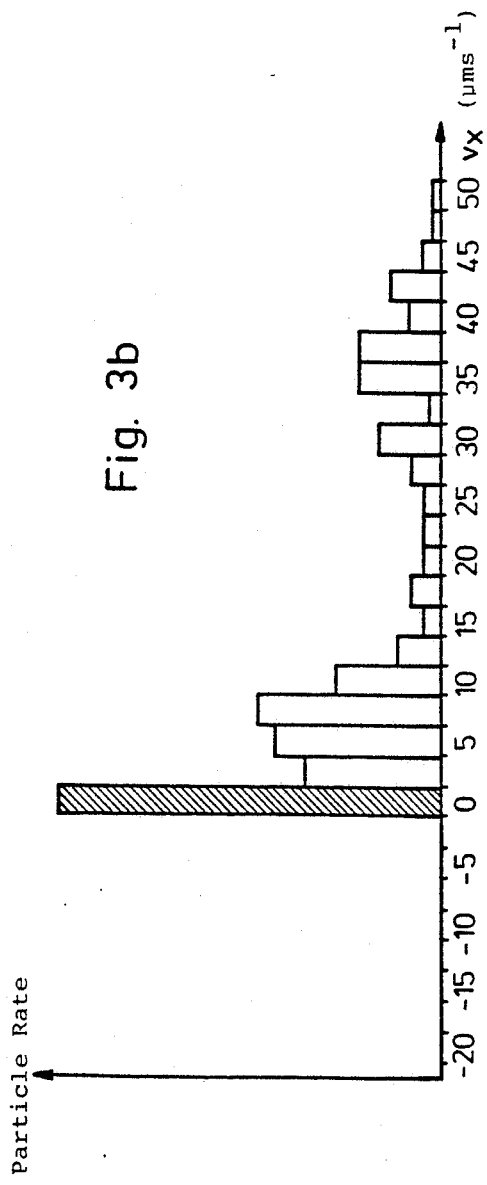

METHOD OF MEASURING THE INTERACTION BETWEEN WALLS AND FLUID

BACKGROUND OF THE INVENTION

1. Field of the Invention

The present invention relates to a method of measuring the interaction of a fluid with the wall delimiting the fluid, comprising illuminating tracer particles and determining their movement with the fluid by measuring the light scattered. The invention also relates to an apparatus for implementing the method thereof.

2. Description of the Background

Certain additives when added to water or aqueous solutions cause these liquids, at a given pressure gradient, to flow through conduits at a considerably greater speed than in the absence of the additives thereof (e.g., ethylene oxide derivatives, polyacrylamides). Encompassed is also an effect called "drag reduction" which is efficiently utilized in the industry, for example, in fire fighting, to increase the volume of streams in waste water channel networks subjected to sudden loads or for increasing the speed of ships and underwater projectiles. Polyisobutylenes produce drag reduction in oils and are used to reduce the pumping output—to 80%—in pipelines. Such reduction of flow resistance occurs not only at supercritical Re numbers but also in laminar streams. For supercritical Re numbers, the reduction in resistance is explained as an attenuation of turbulence, and thus of turbulent energy production and dissipation in the interface layer at the wall as well as in the free stream. For laminar streams, this is explained on the assumption that the fluid layer in contact with the wall already moves at a finite velocity so that the velocity profile deviates toward higher values compared to the velocity profile of water, thus resulting in slipping. The water profile corresponds to the "theoretical" velocity profile calculated with assumed adhesion (non-slip) conditions for streams which are not otherwise influenced by fluid/wall interactions.

Conversely, under certain flow conditions, the same polymers are also able to increase flow resistance. For example, the addition of about 100 ppm Praestol to streams produces an increase in flow resistance of up to 30 times the value for pure water. These increased pressure losses are explained by assuming an absorption of energy by the macromolecules when they expand in acceleration regions (expansion streams) and not by wall effects. Reference points exist which indicate that an increase in the resistance of other fluids (gelatine solutions) can also be produced by wall effects, namely by a phenomenon opposite to slipping, i.e., a delay of the stream near the walls which results in sticking.

Experimental tests with anionic Praestol which is a macromolecular electrolyte indicate that for low Re number streams this behavior is not only a function of the concentration, and thus of the viscosity of the macromolecules, but also of their charge state. Such behavior, therefore, changes considerably with the concentration of strong electrolytes and with the pH of the solvent.

A question can be posed of whether interactions with the walls resulting in slipping or sticking also occur in blood or blood plasma. In such a case, changes in the pH and the electrolyte composition could have an effect on blood flow. In the larger blood vessels, changes in flow near the walls could influence the mechanical stress on the endothelium but could also have an effect on thrombocyte adhesion. In the capillary system, expanded flow would have an effect primarily on the volume of streams. Whether such mechanisms could play a part in circulatory malfunction and also in the physiological control of capillary circulation remains to be studied.

SUMMARY OF THE INVENTION

It is an object of the present invention to provide a method with which to study, for example, velocity profiles in tubular streams of blood plasma and to compare solutions under the influence of the volume stream, the pH of the plasma and the coating of living endothelium cells on the glass wall. For the present purposes, Praestol is used as a comparison solution in which slipping can be reliably detected.

It is a further object of the invention to provide an apparatus with which the described wall influences on the flow can be explained. Thus, it is necessary to observe by direct experimentation the flow occurrences in the direct vicinity of the wall. Reference values for the requirement of high local resolution are the distances d from the wall spacing which are small ($d < 2\mu m$) compared, for example, with the diameter of a thrombocyte.

The above and other objects are attained by the method of the invention for measuring the interaction of a fluid with wall bounding the fluid which comprises placing tracer particles in the fluid, illuminating the particles, and measuring the movement of the particles by means of scattered light, the improvement wherein said step of illuminating comprises illuminating a region of the fluid adjacent the wall at a distance of less than about 1 micron from the wall with a light beam directed towards the interface of the fluid and the wall, so that said light beam is completely reflected; and said step of measuring comprises recording the scattered light images resulting from the motion of the tracer particles in the region and evaluating the motion of the fluid adjacent the wall.

The above and other objects are also attained by the apparatus of the invention for measuring the interaction of a fluid with a wall bounding the fluid by placing tracer particles in the fluid, illuminating the particles, and measuring the movement of the particles by means of scattering light, said apparatus comprising a conduit with a wall to contain a fluid;

a fluid flowing through the conduit, said fluid containing tracer particles; and means for producing a laser beam coupled through the wall into the interface between the fluid and the wall at an angle of complete reflection ($\theta$); and a direct-light dark-field microscope, said microscope for detecting light scattered by the tracer particles and positioned to view a region of the fluid illuminated by the beam.

A more complete appreciation of the invention and many of the attendant advantages thereof will be readily perceived as the same becomes better understood by reference to the following detailed description when considered in connection with the accompanying figures.

BRIEF DESCRIPTION OF THE DRAWINGS

FIG. 2 is a graph of the velocity profile of the "slip" region Vx versus d.

FIGS. 3a and 3b are velocity histograms for pure water and Praestol, respectively.

Figure 1:
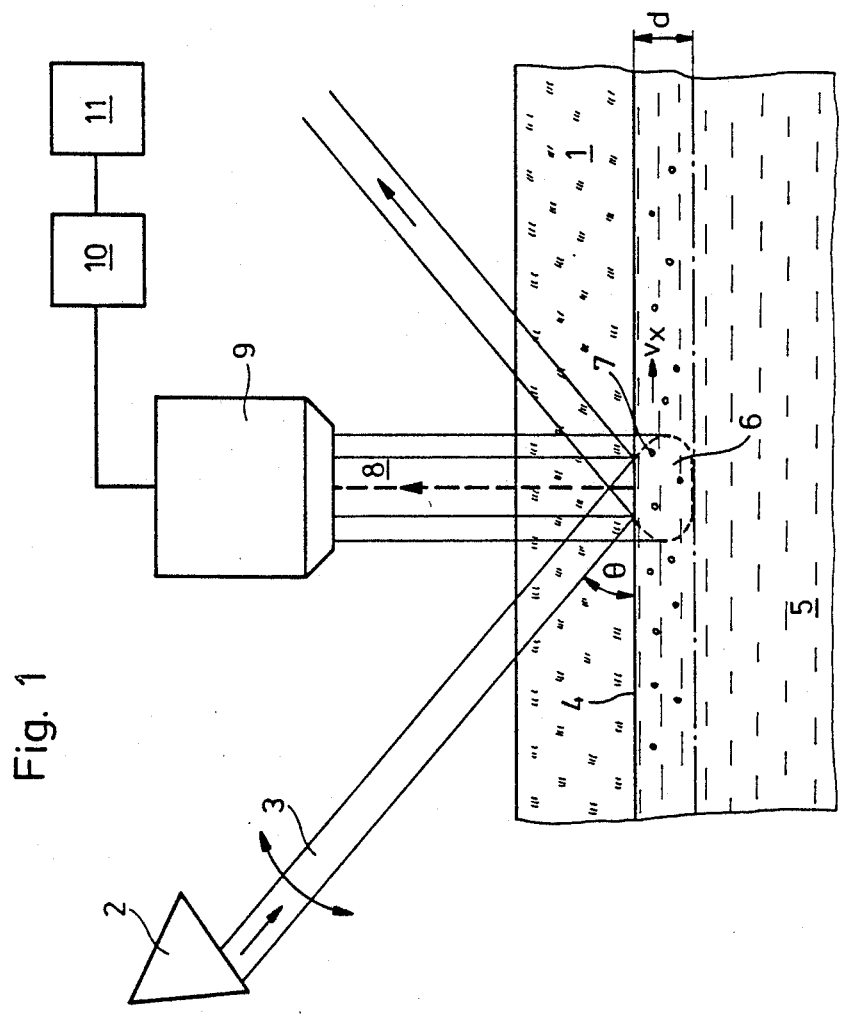
FIG. 1 is a schematic illustration of the method of the invention.

Other objects, advantage and features of the present invention will become apparent to those skilled in the art from the following discussion.

DESCRIPTION OF THE PREFERRED EMBODIMENTS

A method for increasing resolution is required for precise detection since the rheologic phenomenon of slipping occurs in a layer of a thickness of $<1$ $\mu$ adhering to a wall. Total reflection microscopy is one such method. As indicated in the schematically illustrated optical device of FIG. 1, a monochromatic laser light 3 ($\lambda = 0.6328$ $\mu$m) is coupled by means of a prism 2 into the wall 1 of, for example, a glass capillary having a rectangular cross section. With a sufficiently flat angle of incidence $\theta$, total reflection occurs at the interface 4 between glass 1 and fluid 5. The light intensity does not abruptly drop to zero in a region 6 at interface 4, but does so according to an exponential function such that the penetration depth d of the light into the fluid can be defined by the drop in intensity to 1/e. If submicroscopically small tracer particles 7 of gold ($\phi \leq 0.1$ $\mu$m) are now mixed with fluid 5, scattering 8 of light is observed only at those particles 7 which flow in the illuminated layer.

The thickness d of the illuminated layer can be varied by changing the angle of incidence $\theta$. The thickness d of the illuminated layer can be varied between 0.1 $\mu$m and 0.6 $\mu$m with the type of glass employed for capillary and coupling prism (e.g., Kronglas BK 7). The depth resolution capability is no longer determined by the microscope lens 9 but mostly by the thickness d of the illuminated layer 6. Thus, the depth capability resolution can thereby be improved up to 0.1 $\mu$m.

Preliminary tests employing a 0.25% Praestol solution at penetration depths of 0.15 $\mu$m and 0.3 $\mu$m indicate that this method can be used. The laser differential microanemometer employed is a direct light-dark field microscope. The scattered light 8 from tracer particles 7 received by microscope lens 9 is recorded by means of a video recorder 10 and the movement of the particle image is measured by means of individual image evaluation 11 to provide the average velocity $V_x$ over 35 $\mu$m.

Individual image evaluation 11 indicated that for all fluids 5 being examined the motion of the particles 7 carried along in the stream is not stationary in its microscopic dimension but exhibits irregular changes in direction and velocity. The deviation from the average path reaches a maximum of 0.7 $\mu$m per field for water and plasma and 0.3 $\mu$m per field for Praestol. The change in velocity reaches a maximum of 30 $\mu$m/s for water, 30 $\mu$m/s for plasma and 15 $\mu$m/s for 0.25% Praestol solutions. Thus both values decrease with increasing viscosity. The unordered motion must be considered separately in examining rheological influences of fluid/wall interaction, since these velocities are equivalent to the average flow velocities $V_x$ in the region near the wall.

However, only the velocity components $V_x$ are evaluated for an analysis of the slipping and sticking effects. Individual particles 7 in the vicinity of wall 1,4 exhibit positive and negative velocities, and may also remain standstill ($V_x=0$). If a directional stream is superimposed, the particles travel simultaneously over the measuring path. That is, in an average over time there are primarily positive velocity values. The frequency distribution of the velocities results in a Gaussian curve having its maximum at the average velocity (in time) for the respective distance from the wall (velocity histogram).

Observations show that tracer particles 7 still rest at some distance from wall 1, 4, because the polymer molecules adhere to wall 1 and form a layer of 0.1 $\mu$m to 0.4 $\mu$m in thickness, depending on volume stream, charge and concentration of the molecules. At the interface $d'=0$ between quiescent layer and flowing fluid 5, which phase interface has been pushed forward into the lumen by this amount, flow velocities from $V_0=0$ $\mu$ms$^{-1}$ to the slip velocity $V_0=V_s$ were measured.

Particles 7 preferably move at either a high or a very low velocity. Some particles 7 move steadily whereas others are temporarily braked to $V=0$ and are accelerated again after periods of adhesion of different duration. Each individual tracer particle 7 is able to successively take on each one of these velocities. Clearly, the increase in velocity from $V_0=0$ to $V_s$ occurs during an interval d which is smaller than the resolution limit of the process (d $<0.15$ $\mu$m). Clarification is thus obtained indirectly by way of the velocity profile in the "slip" region $V_x$ over d (see FIG. 2).

For wall distances which vary with the concentration and degree of stiffening between $d \leq 0.1$ $\mu$m and $d \approx 0.4$ $\mu$m, the velocity abruptly jumps to the value of the slip velocity. The different velocities can thus be associated with different distances from the wall. Since the transition interval is very small ($\approx 0.1$ $\mu$m), extremely high shear velocities result for the slip interval, as indicated by the velocity profile for the region near the wall which has been determined from these data in a first approximation (FIG. 2). However, the actual jump in velocity up to the slip velocity does not occur in the layer immediately adjacent to wall 1, 4 but within fluid 5.

The velocity profile shown in FIG. 2 for a rough estimate of a 0.25% Praestol solution during the interval $d=0$ to $d=0.1$ $\mu$m and $\dot{V}=2.9$ $10^{-2}$mlh$^{-1}$, is based on the velocity histogram (FIGS. 3a-b) and control measurements with a total reflection microscope (FIG. 1).

The velocity profile of water at $d<1$ $\mu$m is a linear extrapolation, i.e., a theoretical curve. The velocity could not be measured since the amplitudes of the Brownian molecular motion in the y direction are very large when compared to the thickness of the illuminated layer. Sticking to the wall, in conjunction with the slip phenomenon, produces a turning point profile. In the slip region, D=125 s$^{-1}$($\eta=13$ cP) At a slip velocity V=90 $\mu$ms$^{-1}$, D=475 s$^{-1}$(not shown). The hatched circle illustrates the cross section of the non-solvatized tracer particles 7.

The velocity $V_x$ of individual particles 7 at the interface between the adhering layer and the free solution was measured in time intervals of 40 ms and it was recorded how many particles 7 had what velocity. A Gaussian distribution having a maximum at the calculated velocity is obtained in a stream of pure water (FIG. 3a) for this wall distance due to the superposition of Brownian molecular motion on the flow velocity.

With the addition of Praestol (FIG. 3b), however, a curve is obtained which has three peaks. The measurement at Q=29 $\mu$hl$^{-1}$ shall serve as an example. With $V_0=32$ $\mu$ms$^{-1}$, one of the maxima corresponds to the slip velocity. A further maximum lies at $V_0=0$ $\mu$ms$^{-1}$. The high frequency and duration of the events at $V_0=0$ speaks for great adhesion at the surface of the quiescent layer and thus for the validity of the sticking condition. This peak is followed by a secondary maximum at $V_0=1.4$ $\mu ms^{-1}$ to 3 $\mu ms^{-1}$. These values are only slightly higher than the velocity calculated on the basis of the flow curve for a distance $d'=0.15$ $\mu m$ from the surface of the quiescent layer.

An assumption can be made that two discretely different and finite velocities are to be associated with different distances from the wall which lie within the measuring range of 0.15 $\mu m$, and that the motion of the gold particles 7 approximately correctly represents the motion of fluid 5. In this situation, the conclusion can be drawn that near the adhering layer 4, fluid 5 flows at the calculated velocity. Consequently, the jump in velocity to $V_s$ does not occur at the surface of the adhering layer but within the free fluid.

The thickness d of the fluid layer in which slipping takes place is less than $d=0.15$ $\mu m$ (particle diameter). The viscosity in the slipping layer can be estimated from the shear velocities $D_s$ in the slip region whose width is assumed to be 0.1 $\mu m$ for the calculation if the shear stress is known. Almost independently of $D_s$, the viscosity is about 4 cP and is less by a factor of 7 to 36 than the viscosity measured in the rheometer for the same shear velocity. This indicates a change in the fluid 5, e.g., a split of the polymer molecules under the influence of high shear forces or demixing of the polymer solution so that the flow characteristics in the slip region would be determined by a highly diluted polymer solution (or the water solution) if one assumes that the width of the slip interval is less than 0.1 $\mu m$.

Example for a measurement of the viscosity of the fluid within the slip layer

Materials and Methods

Polymer solutions

To prepare the aqueous solutions of anionic polyacrylamides (Praestol K 2515 Fa. Stockhausen) at a concentration of 0.030 percentage by weight, the dry polymer was dispersed within water at 20° C. room temperature by stirring slowly (10 cpm) overnight. Spontaneous swelling serves for further dissolution. The concentration $c_o=0.3\%$ was not corrected for the water content of the dry polymer (8–10%)[4]. The flow experiments were generally performed using 24 h to 48 hold solutions (pH 7.2). It should be mentioned that the dissolution is still incomplete as indicated by local inhomogeneities in the refractive index of these solutions. According to the producer's reference the proportion of ionogen (Na-acrylate) to non-ionogen groups is 15:85; the molecular weight is estimated to $M_w=12\,000\,000 g/Mol$. For ionogen polyacrylamides in 10% aqueous NaCl solution the parameters (K,$\alpha$) of the Mark-Houwink-Sakurada relation and the intrinsic viscosity $\eta$ were estimated by Korotkina et al.[4] as follows $$[\eta]=K\,M_w{}^\alpha=3.09\,10^2 M_2{}^{0.67}$$

Performance of capillary tube flow experiments

The solutions were used to perfuse straight rectangular glass capillaries (width=100 $\mu m$, height=1000 $\mu m$, length=$5.10^4$ $\mu m$; microslides Fa. Camlab, Cambridge). Scanning electron microscopic investigations revealed the roughness of the inner surface of the glass capillaries to smaller than 0.01 $\mu m$. The volume flow rate Q was controlled by means of a syringe pump (Perfusor, Fa. Braun-Melsungen) and held constant at various levels ranging between $Q=2.5$ $\mu l\,h^{-1}$ and $Q=145$ $\mu l\,h^{-1}$, the corresponding maximal velocities within the center of the capillary channel are $v_{max}=20$ $\mu m\,s^{-1}$ to $v_{max}=170$ $\mu m\,s^{-1}$, respectively.

The velocity profiles were measured in the central plane (defined by the optical and the capillary axis) and at a distance of $2.5\times 10^4$ $\mu m$ from the orifice of the capillary (500-fold hydraulic diameter calculated from the cross sectional area and the circumference of the capillary). The width to height ratio of the rectangular capillary was 10.0 which is considered to be sufficient for the development of a fully developed two-dimensional flow, field.

Evaluation of slip velocity $v_s$ and wall shear stress $\tau_w$

The smallest distance d, from the wall at which velocities could be measured with the anemometer described is limited by the axial resolution which is determined mainly by the "diameter of the tracer particles" and was approximately 0.15 $\mu m$. The velocity $v_o$ at the interfacial boundary could, therefore, only be computed by extrapolation of the velocity profile to the wall position $d=0$. For this purpose the following equation was fitted to the experimentally determined velocity profile:

$$(v-v_o):(v_{max}-v_o)=1-(y/R)^n \quad (1)$$

($v_{max}$=measured velocity at the tube axis, y=radial distance from the tube axis, R=half diameter of the tube, R=50 $\mu m$, n=parameter calculated from the flow curve which was measured by a low shear viscosimeter, Rheomat-30, Fa. Contraves).

To calculate the wall shear stress $\tau_w(=\eta.D_w)$ the wall shear rate $D_w$ was determined from the slope of the velocity profile at $d=0$. The value of the dynamic viscosity was taken from the flow curve measured for the fluid examined.

Results

Because the volume flow rate was controlled, the velocity profiles measured at identical values of volume flow rate can directly be compared for different fluids. The velocity profiles are adequately described by the equation (1); the exponent n varies between $n=2$ for water (parabolic profile) and $n=3.38$ for a Prestol solution of 0.30 percentage by weight. For water the velocity $v_o$ at the wall position was determined to be zero, whereas finite values of $v_o$ were obtained for the Praestol solution (FIG. 1). This result indicates that for these solutions a slip-phenomenon occurs at distances $d<0.15$ $\mu m$ from the wall ($v_o$=slip velocity $v_s$). However, the slip velocity $v_s$ cannot be calculated in advance applying the viscosity data from the measured flow curve.

In order to determine the dependence of the slip velocity $v_s$ on the wall shear stress $\tau_w$, the latter was varied by stepwise changing the volume flow rate Q. A variation of Q between 18.0 $\mu l\,h^{-1}$ and 54.0 $\mu l\,h^{-1}$ causes a variation of $\tau_w$ between 1.5 dyn cm$^{-2}$ and 3.2 dyn cm$^{-2}$ (correlated with the variation of Q are changes of the longitudinal pressure gradient $\Delta p$). For each setting of Q the velocity profile was measured. The result is a series of velocity profiles with Q (or $\tau_w$ resp.) as series parameter.

By increasing Q in the range described the slip velocity increases from 30.7 $\mu m\,s^{-1}$ to 58 $\mu m\,s^{-1}$. The relationship between slip velocity $v_s$ and shear stress $\tau_w$ turned out to be linear ($v_s=\sigma.\tau_w$) with $\sigma$, the slip-coefficient, as a constant value for a given Praestol concentration. The straight line demonstrating this function intersects the $v_s/\tau_w$ coordinate system at zero (within the concentration range $0.05\% \leq c_o \leq 0.4\%$ the value of $\sigma$ decreases linearly with increasing $c_o$) The slip coefficient for the 0.30% Praestol solution was determined to be $\sigma = 1.9 \cdot 10^{-4} \text{cm}^3 \text{dyn}^{-1} \text{s}^{-1}$. The values of $\sigma$ are in quantitative good agreement with the respective value ($\beta$) calculated by Brunn in a theoretical study.

The linear relationship $\tau'_w$ and $v_s$ shows, that the quotient $\eta/\delta$ remains constant (eq. 2; $\delta$, width of the fluid layer, in which the "slippage" takes place).

$$\tau_w = \frac{\eta}{\delta} v_s = \text{const. } v_s$$

From the assumption that both parameters $\tau$ and $\delta$ are constant (the simplest explanation for the fact that $\tau/\delta$ is constant), it follows: 1. that the Praestol solution does not glide directly along the wall, but by mediation of a Newtonian fluid of low viscosity lining the wall surface and 2. that the width $\delta$ of this slipping fluid layer may be almost constant.

The velocity histograms (FIG. 3a-c) show that the non slip condition is valid for the polymer flow. If $\delta$ is assumed to be 0.1 μm, the shear rate Ds within the slipping fluid layer can be evaluated. The difference between Dw and Ds for a given $\tau_w$ indicates that the viscosity $\eta_s$ of the slipping fluid is much lower than the viscosity values obtained from the flow curve; $\eta_s 32 \tau_w/\text{Ds} = 5.28$ cP for the 0.3% Praestol solution. From the viscosity $\eta_s$ the polymer concentration $c_s$ of the slipping fluid can be estimated on the basis of a family of flow curves with he polymer concentration $c_o$ as series parameter. The difference $c_o - c_s$ allows an estimation of the chemical potential responsible for the reduction of polymer concentration of the slipping fluid.

Figure 4:
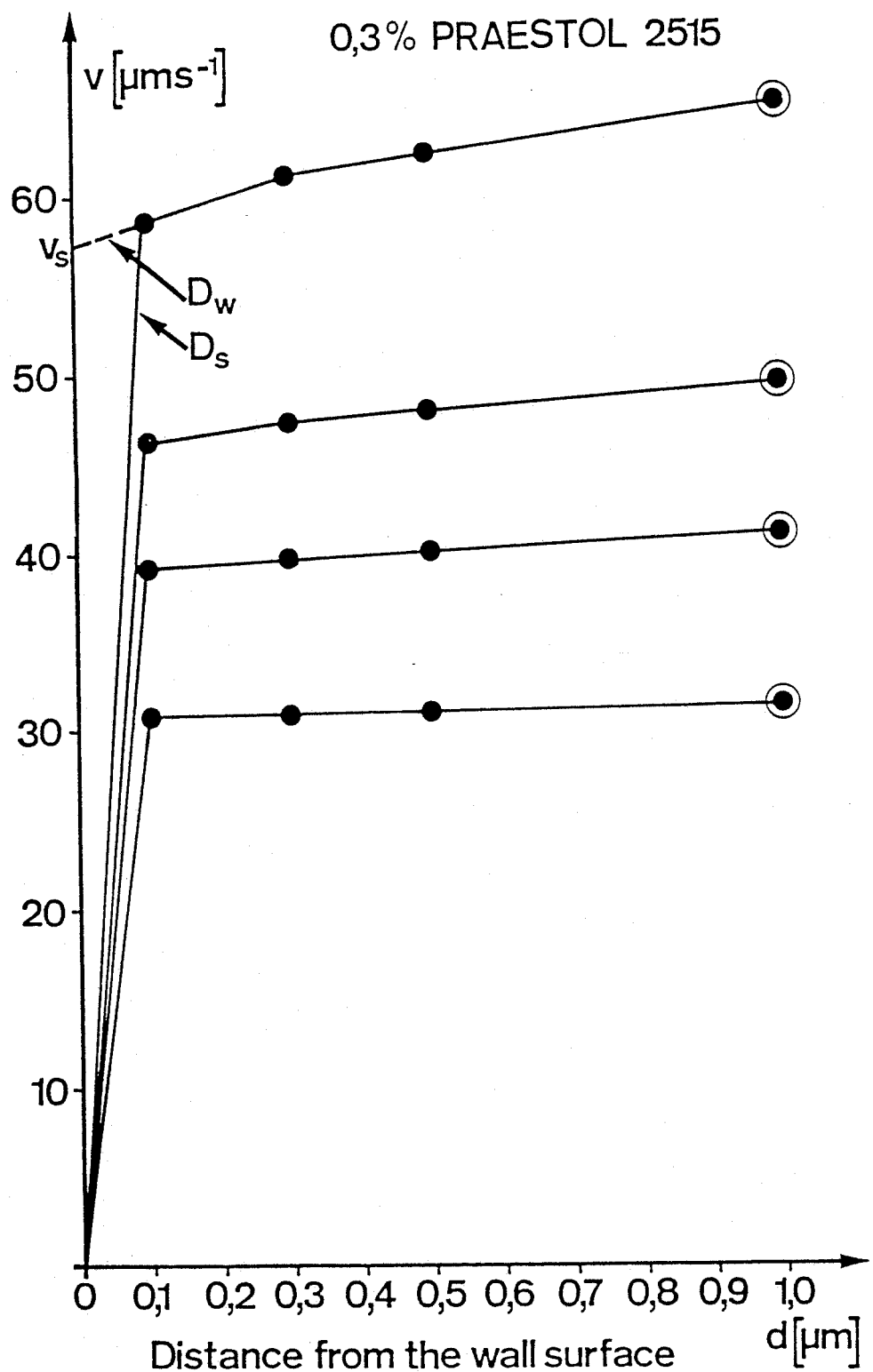
FIG. 4 is a family of velocity profiles measured by the method of the invention with volume flow rate or shear stress as the series parameter.

FIG. 4 illustrates a family of velocity profiles with Q(or $\tau_w$ resp.) as series parameter. Q was impressed on the following values (in μl min$^{-1}$): 0.30; 0.45; 0.60; 1.00. The highest steepness of Ds compared to Dw (obtained from extrapolation) indicates that the viscosity within the slipping flow is lower compared to that of the bulk flow. In FIG. 4, the dots indicate values measured by a total reflection anemometer (TRA) and the circles indicates measured by a laser micro anemometer (LMA).

The present disclosure relates to the subject matter disclosed in application No. P 35 43 108.3, filed in Republic of Germany on Dec. 6, 1985, the entire specification of which is incorporated herein by reference.

The invention now being fully described, it will be apparent to one of ordinary skill in the art that many changes and modifications can be made thereto without departing from the spirit or scope of the invention as set forth herein.

What is claimed is:

1. In a method of measuring the interaction of a fluid having a shear stress value with a wall bounding the fluid which method includes placing tracer particles in the fluid, illuminating the particles, and measuring the movement of the particles by means of scattered light, the improvement wherein:

said step illuminating comprises illuminating a region of the fluid adjacent the wall at a distance of less than 1 micron from the wall with a light beam directed towards the interface of the fluid and the wall so that the light beam is completely reflected;

said step of measuring comprises recording the scattered light images resulting from the motion of the tracer particles in the region and evaluating the motion of the fluid adjacent the wall; and the method further comprising the step of calculating the viscosity of a slipping layer of the fluid located next to the interface with the said of the shear stress value.

2. The method of claim 1, further comprising varying the distance from which the light beam illuminates the region between the fluid and the wall by changing the angle of incidence of the light beam.

3. An apparatus for measuring the interaction of a fluid with a wall bounding the fluid by placing tracer particles in the fluid, illuminating the particles, and measuring the movement of the particles by means of scattered light, said apparatus comprising:

a conduit with a wall to contain a fluid;

a fluid flowing through the conduit, said fluid containing tracer particles; and means for measuring the interaction of said fluid with said wall, including:

means for producing a laser beam coupled through the wall into the interface between the fluid and the wall at an angle of complete reflection (), a direct-light dark-field microscope, said microscope for detecting light scattered by the tracer particles and positioned to view a region of the fluid illuminated by the beam, and means, coupled to said microscope, for calculating the movement of the particles on the basis of the light detected by said microscope.

4. The apparatus of claim 3, further comprising a video recorder coupled between said calculating means and said microscope, said recorded for recording an ultramicroscopic image of the tracer particles and being operatively connected to said microscope to permit an individual evaluation of the recorded images.

5. In a method of measuring the interaction of a fluid with a wall bounding the fluid which method includes placing tracer particles in the fluid, illuminating the particles, and measuring the movement of the particles by means of scattered light, the improvement wherein:

said step of illuminating comprises illuminating a region of the fluid adjacent the wall at a distance of less than 1 micron from the wall with a light beam directed towards the interface of the fluid and the wall so that the light beam is completely reflected;

said step of measuring comprises recording the scattered light images resulting from the motion of the tracer particles in the region and evaluating the motion of the fluid adjacent the wall; and the method further comprising the step of calculating a characteristic of the fluid located next to the interface based on the images recorded during said step of measuring.

6. A method as in claim 3, wherein said step of calculating comprises the step of calculating the characteristic of a slipping layer of the fluid located next to the interface.

* * * * *

UNITED STATES PATENT AND TRADEMARK OFFICE
CERTIFICATE OF CORRECTION

PATENT NO. : 4,804,268
DATED : February 14th, 1989
INVENTOR(S) : Helmut Müller-Mohnsen et al It is certified that error appears in the above-identified patent and that said Letters Patent is hereby corrected as shown below:

In the heading of the patent, under [75], the name of the first inventor should read --Helmut Müller-Mohnsen--.

Item [19] should read -- Müller-Mohnsen et al.

Signed and Sealed this

Fifteenth Day of August, 1989

Attest:

DONALD J. QUIGG

Attesting Officer

Commissioner of Patents and Trademarks